US006830566B2

(12) United States Patent
Kuen et al.

(10) Patent No.: US 6,830,566 B2
(45) Date of Patent: Dec. 14, 2004

(54) PROCESS FOR MAKING ABSORBENT ARTICLES WITH SINGLE-PIECE PANELS

(75) Inventors: David Arthur Kuen, Neenah, WI (US); John Irvin VanDeurzen, Kimberly, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 30 days.

(21) Appl. No.: 10/038,175

(22) Filed: Oct. 23, 2001

(65) Prior Publication Data

US 2002/0058918 A1 May 16, 2002

Related U.S. Application Data

(62) Division of application No. 09/290,953, filed on Apr. 13, 1999, now Pat. No. 6,352,607.

(51) Int. Cl.[7] .................................................. A61F 13/15
(52) U.S. Cl. ...................... 604/396; 604/386; 604/387; 604/389
(58) Field of Search ................................. 604/396, 392, 604/385.01, 385.24, 385.27, 385.29, 385.3, 386–389

(56) References Cited

U.S. PATENT DOCUMENTS

| 1,494,044 A | 5/1924 | Ward et al. | |
|---|---|---|---|
| 1,998,140 A | 4/1935 | Loew | 2/224 |
| 2,397,641 A | 4/1946 | Blair | 2/43 |
| 2,435,945 A | 2/1948 | Redmond | 2/224 |
| 2,538,596 A | 1/1951 | Sheridan | 2/224 |
| 2,596,127 A | * 5/1952 | Carmean | 604/396 |
| 3,087,495 A | 4/1963 | Hart | 128/528 |
| 3,142,301 A | 7/1964 | Erteszek | 128/528 |
| 3,368,563 A | 2/1968 | Scheier | 128/288 |
| 3,687,141 A | 8/1972 | Matsuda | 128/288 |

(List continued on next page.)

FOREIGN PATENT DOCUMENTS

| EP | 580 422 | 3/1996 | ............ A41B/9/00 |
|---|---|---|---|
| EP | 516 905 | 5/1996 | ............ D04B/1/24 |
| GB | 1 520 740 | 8/1978 | ............ A41B/13/02 |
| JP | 52-64128 | 5/1977 | ............ A41B/13/04 |
| WO | 94/09736 | 5/1994 | ............ A61F/13/15 |
| WO | WO 94/09736 | * 11/1994 | ............ A61F/13/15 |
| WO | 96/23920 | 8/1996 | ............ D04B/1/24 |
| WO | 97/36566 | 10/1997 | ............ A61F/13/62 |

*Primary Examiner*—John J. Calvert
*Assistant Examiner*—Jacqueline F. Stephens
(74) *Attorney, Agent, or Firm*—Pauley Petersen & Erickson

(57) ABSTRACT

A process and apparatus for making pant-like disposable absorbent garments with single-piece elastic side panels, and garments so made, are provided. The single-piece side panels eliminate the additional cost associated with multi-part side panels, and improve aesthetic appearance of the garments by eliminating side seams. The process and apparatus accomplish the steps of providing a garment chassis having unfinished lateral edges, folding the chassis so that a front portion overlaps a back portion, and folding and bonding the single-piece side panels so that opposing of the side panels are joined to the lateral edges on the garment chassis.

13 Claims, 5 Drawing Sheets

U.S. PATENT DOCUMENTS

| | | | |
|---|---|---|---|
| 3,720,212 A | 3/1973 | Kaupin | 128/288 |
| 3,901,236 A | 8/1975 | Assarsson et al. | 128/284 |
| D245,546 S | 8/1977 | Okuda | D2/10 |
| 4,076,663 A | 2/1978 | Masuda et al. | 260/17.4 GC |
| 4,286,082 A | 8/1981 | Tsubakimoto et al. | 526/240 |
| 4,302,853 A | 12/1981 | Mesek | 2/402 |
| 4,560,381 A | 12/1985 | Southwell | 604/396 |
| 4,650,530 A | 3/1987 | Mahoney et al. | 156/73.1 |
| D290,060 S | 6/1987 | Leo | D2/10 |
| 4,690,681 A | 9/1987 | Haunschild et al. | 604/396 |
| 4,940,464 A | 7/1990 | Van Gompel et al. | 604/396 |
| 4,972,525 A | 11/1990 | Hwang | 2/406 |
| 4,984,304 A | 1/1991 | Brown | 2/401 |
| D315,050 S | 3/1991 | Bush et al. | D2/10 |
| 5,046,272 A | 9/1991 | Vogt et al. | 38/143 |
| 5,087,255 A | 2/1992 | Sims | 604/385.1 |
| 5,204,997 A * | 4/1993 | Suzuki et al. | 2/400 |
| 5,255,393 A | 10/1993 | Brady | 2/409 |
| 5,440,764 A | 8/1995 | Matsushita | 2/401 |
| 5,496,298 A * | 3/1996 | Kuepper et al. | 604/389 |
| 5,535,452 A | 7/1996 | Rozenblat | 2/403 |
| 5,554,145 A * | 9/1996 | Roe et al. | 604/385.3 |
| 5,591,155 A | 1/1997 | Nishikawa et al. | 604/393 |
| 5,595,618 A | 1/1997 | Fries et al. | 156/164 |
| 5,759,340 A | 6/1998 | Boothe et al. | 156/519 |
| 5,830,206 A | 11/1998 | Larsson | 604/390 |
| 5,906,008 A * | 5/1999 | Heki et al. | 2/400 |
| 6,113,717 A | 9/2000 | Vogt et al. | |

* cited by examiner

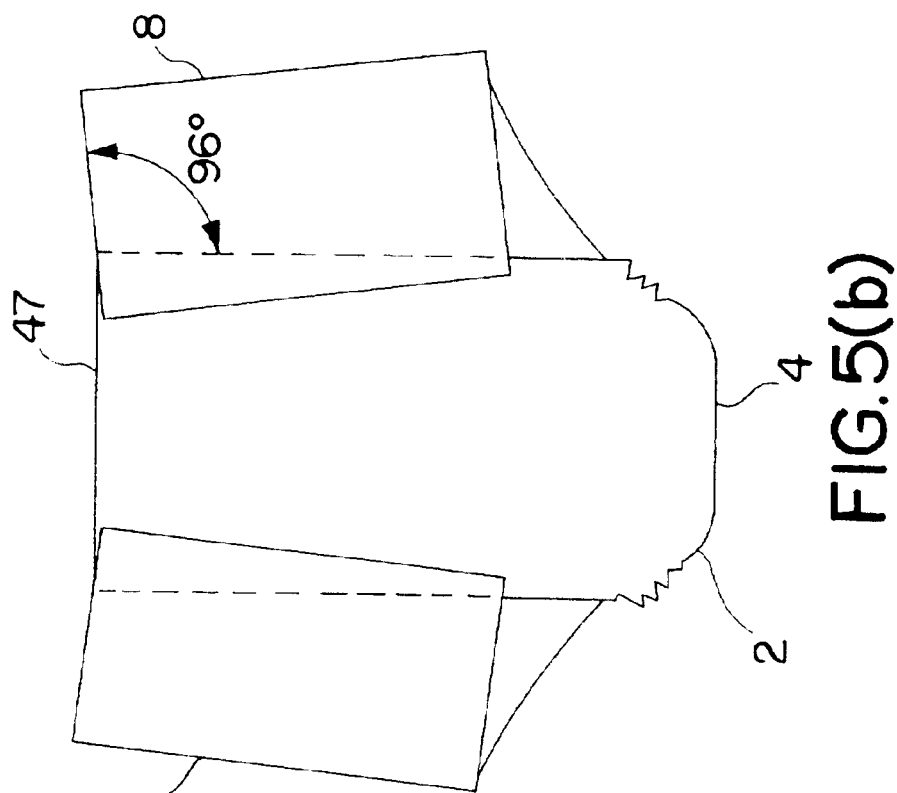
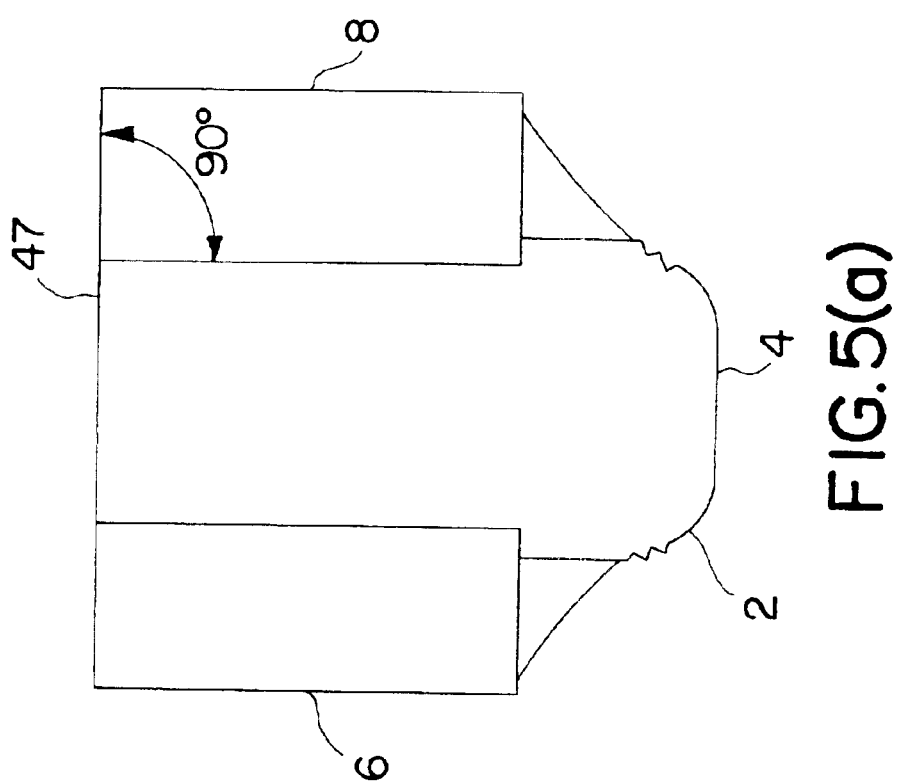

PROCESS FOR MAKING ABSORBENT ARTICLES WITH SINGLE-PIECE PANELS

CROSS REFERENCE TO RELATED APPLICATION

This application is a divisional of patent application Ser. No. 09/290,953, filed on 13 Apr. 1999. now U.S. Pat No. 6,352,607, Mar. 5, 2002.

FIELD OF THE INVENTION

This invention is directed to a process and apparatus for making pant-like disposable absorbent garments with single-piece elastic side panels, and to absorbent articles so made. The process eliminates the extra cost and material required to make similar absorbent articles with multi-piece side panels, joined together with seams.

BACKGROUND OF THE INVENTION

Disposable absorbent garments having a pant-like configuration are used for child training pants, adult incontinence garments, diapers, swimsuits and the like. Referring to FIG. 1, a prior art pant-like absorbent garment 2 includes a waste containment section ("chassis") 4 and two side portions 6 and 8 defining a waist opening 10 and a pair of leg openings 12 and 14. The side panel 6 includes stretchable panels 18 and 20 joined together at seam 30. The side panel 8 includes stretchable panels 24 and 26 joined together at seam 32. Seams 30 and 32 extend longitudinally from the waist opening 10 to the leg openings 12 and 14 of the garment 2.

The waste containment section 4 includes front and back portions 5 and 7, and central ("crotch") region 15. Chassis 4 includes multiple layers (not shown) including, for instance, a liquid-permeable top layer, an absorbent core layer, and a liquid-impermeable outer cover layer 16 which faces away from the wearer. The waste containment section 4 also includes elasticized waist portions 22 on the front and back of the garment. The leg opening portions 12 and 14 also include elastic portions 46 which extend substantially around the portion of the leg openings defined by the waste containment section 4.

The disposable garment also includes leak guards in both leg openings, which help prevent lateral leakage of waste material through the leg openings. The leak guards have commonly been provided by elasticized flap portions 50 which are connected to the interior of the garment along the lower part of each leg opening. During use, the elasticized flap portions 50 fit snugly against the wearer and effectively block most spillage of waste material from the leg openings.

The use of stretchable side panels 6 and 8 having two or more parts per panel, joined at seams, results from a conventional manufacturing process. In the conventional process, the absorbent garments are initially manufactured as a single, flat piece which is then folded over and connected at the side seams 30 and 32. The disposable absorbent garment industry is cost-competitive, and the side seams represent material and processing which is not essential to the finished product. From a cost standpoint, there is a desire for an inexpensive process for manufacturing disposable absorbent garments having single-piece elastic side panels, thus eliminating the side seams.

SUMMARY OF THE INVENTION

The present invention is directed to a process and apparatus for making a disposable absorbent garment without the side seams, and to a product having seamless, single-piece elastic side panels. The terms "elastic" and "stretchable" include any material which can be stretched, and which tends to return to its original shape when relaxed. The process includes the steps of preparing a waste containment section (also called a "chassis") of the absorbent article using conventional techniques, and folding the chassis so that a front portion is superimposed on a back portion thereof. The term "chassis" essentially means the absorbent article without the side panels. The folded chassis is transported along a conveyor in a machine direction, with the unfinished edges of the chassis substantially aligned with the direction of movement.

As the chassis travels forward, single-piece side panels on both sides of the conveyor are aligned, treated with adhesive along two opposite edges, and partially folded. When the chassis passes the location where the side panels are being processed, the partially folded side panels are completely folded over the edges of the chassis, such that the adhesive binds the edges of the side panels to the overlapped edges of the chassis. A similar result may be achieved using thermal bonding, ultrasonic bonding, or another suitable bonding technique.

The apparatus of the invention includes a rotary cam device having four stations and an internal vacuum chamber. As the cam device rotates, side panels pass through each of the four stations. A first station picks up a properly oriented side panel using a vacuum plate. A second station applies adhesive to the side panel edges. A third station begins to fold the side panel, and a fourth station closes the side panel over the edges of the chassis. The peripheral speed of the cam device is the same as the linear speed of the chassis, and the peripheral distance between each of the four stations is the same as the linear distance between successive chassis on the conveyor. Two rotary cam devices, which are similar but move in opposite directions, are positioned on both sides of the conveyor so that both side panels can be applied in this fashion.

The product of the invention is an absorbent garment similar to the one described above, except that the stretchable side panels are each constructed of a single piece, and without side seams.

With the foregoing in mind, it is a feature and advantage of the invention to provide an inexpensive process for applying single-piece elastic side panels to disposable pant-like absorbent garments.

It is also a feature and advantage of the invention to provide a simple apparatus for accomplishing this result.

It is also a feature and advantage of the invention to provide a relatively inexpensive disposable absorbent article having single-piece side panels, a lower cost of production, and better appearance and fit than similar articles having multiple-piece side panels.

BRIEF DESCRIPTION OF THE DRAWINGS

FIGS. 5(a) and 5(b) illustrate disposable absorbent garments of the invention in which the side panels are mounted at different angles relative to the waistline on the chassis.

DETAILED DESCRIPTION OF THE PRESENTLY PREFERRED EMBODIMENTS

Figure 4:
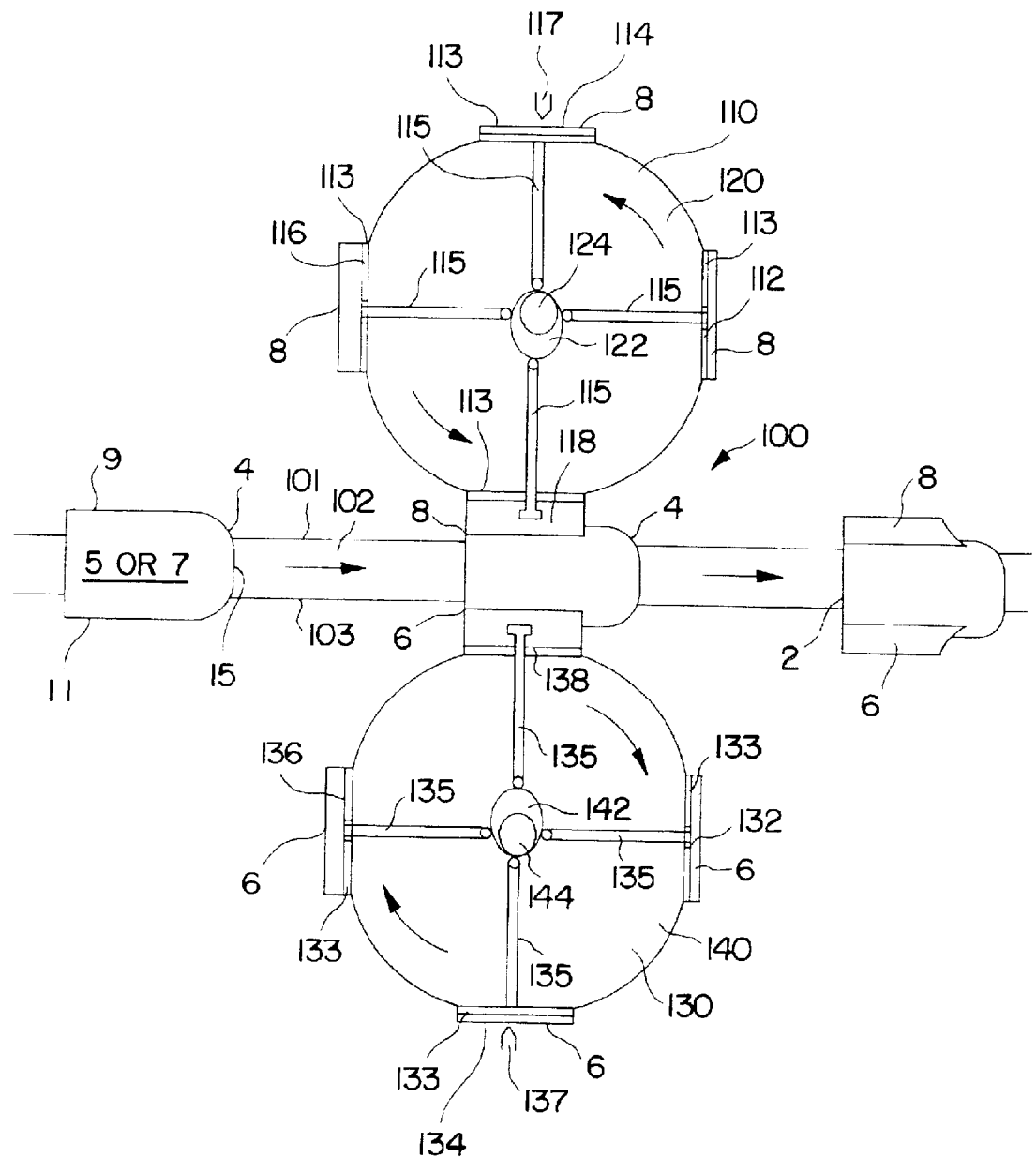
FIG. 4 schematically illustrates an apparatus and process for making the disposable absorbent article of the invention.

Referring first to FIG. 4, an apparatus and corresponding process for making disposable absorbent garments with single-piece side panels are illustrated. Apparatus 100 includes a conveyor 102 which is moving in a direction of travel as shown by the arrows, at a velocity "v". A plurality of chassis 4 of disposable absorbent garments are positioned on the conveyor and spaced from each other in the direction of travel at a constant center-to-center distance "d". Each of the chassis 4 is folded over along a central region 15 which corresponds to the crotch region of the garment, so that either the front portion 5 or back portion 7 of the chassis is tucked under the other and faces conveyor 102, and the other of the front or back portions faces away from conveyor 102 as shown. The conveyor 102 is narrower than the chassis 4, so that edges 9 and 11 of each chassis 4 overhang edges 101 and 103 of conveyor 102. The conveyor 102 is preferably constructed of a porous screen or other porous material, so that a controlled vacuum source (not shown) can be applied underneath the conveyor to maintain the chassis in position on the conveyor.

Each folded chassis 4 has first side edges 9 and second side edges 11 which are aligned substantially parallel to the direction of travel of the conveyor 102. The plural terms "first side edges 9" and "second side edges 11" reflect the fact that each chassis 4, when folded over as in FIG. 4, has an upper (front or back) portion 5 or 7 which is visible, having first edge 9 and second edge 11, and a lower (front or back) portion of equal or similar size and shape folded underneath the upper portion, also having first edge 9 and second edge 11. The disposable garments of the invention may be substantially symmetrical to the front and back of the center region 15, or may have slight differences in width. When folded through the central region 15, the first side edge 9 of the front portion 5 is proximate to (substantially aligned, or slightly offset, with respect to) the first side edge 9 of the back portion 7, and the second side edge 11 of the front portion 5 is proximate to (substantially aligned, or slightly offset, with respect to) the second side edge 11 of the back portion 7.

The apparatus 100 includes two side panel applicators 110 and 130 positioned along sides 101 and 103 of the conveyor. First side panel applicator 110 includes a side panel pick-up station 112, an adhesive applicator station 114, a folding station 116 and a closing station 118. The four stations 112, 114, 116 and 118, as defined, are located 90 degrees apart from each other on a rotatable (preferably cylindrical) housing 120 whose operation is affected by a fixed cam 122 and rotating shaft 124. The housing 120 is sized so that the center-to-center (90 degree) peripheral distance between each of the four stations, defined as $2\pi r/4$ (with "r" being the radius of the housing), is the same as the center-to-center distance "d" between the successive chassis on the conveyor 102. Also, the housing 120 turns in the counter-clockwise direction shown by the arrows, so that its peripheral (linear) velocity is the same as the velocity of the conveyor 102.

The housing 120 includes an internal vacuum chamber capable of pulling vacuum against porous hinged vacuum plates 113 as the housing rotates. Each foldable plate is movable between opened and closed positions by action of extendable and retractable spring-loaded clamping bars 115 whose axial position is driven by fixed cam 122 as housing 120 rotates with drive shaft 124. At the first station 112, the clamping bar 115 is retracted and the porous plate 113 is completely open. Vacuum is pulled on the porous plate 113, causing it to pick up and engage a properly oriented elastic side panel 8 from a supply source (not shown).

As the housing 120 rotates, the plate 113 holding the elastic side panel 8 passes the second station 114 where an adhesive is applied along upper and lower edges of the side panel 8 using, for instance, spray nozzles 117. A wide variety of conventional adhesives (described further below) may be employed. Different methods of adhesive application may also be employed including, for instance, roller printing or brush application.

As housing 120 continues to rotate, plate 113 holding panel 8 passes the third station 116 which, in effect, accomplishes a partial and progressive folding of plate 113 and side panel 8 using a mechanical linkage capable of opening and closing the porous plate 113. At this location, the fixed cam 122 exerts pressure against spring-loaded clamping bar 115, which causes progressive extension of the clamping bar 115 and folding of the plate 113. This progressive folding action continues until the fourth station 118, at which point the clamping bar 115 is completely extended by the cam 122, causing vacuum plate 113 to substantially close, so that the edges of side panel 8 overlap and are clamped onto the first edges 9 of chassis 4. When the clamping is completed, the vacuum holding the side panel to the porous vacuum plate 115 is removed. This may be accomplished, for instance, with an electronic or mechanically controlled air valve. The adhesive causes the edges of the side panel and chassis to remain together and intact, as the finished absorbent garment 2 is transported away from the panel applicators.

The second panel applicator 130, positioned along the conveyor on the side opposite the panel applicator 110, operates in identical fashion except that the rotation of the housing 140 is clockwise (i.e. is opposite the rotation of housing 120 4of first panel applicator 110). Second side panel applicator 130 includes a side panel pick-up station 132, an adhesive applicator station 134, a folding station 136 and a closing station 138. The four stations 132, 134, 136 and 138, as shown, are located 90 degrees apart from each other on a rotatable (preferably cylindrical) housing 140 which is affected by a fixed cam 142 and a rotating shaft 144. Housing 140 is sized so that the center-to-center (90 degree) peripheral distance between each of the four stations, defined as $2\pi r/4$ (with "r" being the radius of the housing) is the same as the center-to-center distance "d" between the successive chassis on the conveyor 102. Housing 140 turns in the clockwise direction shown by the arrows, so that its peripheral (linear) velocity is the same as the velocity of conveyor 102.

Housing 140 includes an internal vacuum chamber capable of pulling vacuum against porous foldable vacuum plates 133 as the housing rotates. Each foldable plate is moveable between opened and closed positions by action of extendable and retractable spring-loaded clamping bars 135 whose axial position is driven by fixed cam 142 as housing 140 rotates with drive shaft 144. At the first station 132, the porous plate 133 is completely open. Vacuum is pulled on the porous plate 133, causing it to pick up and engage a properly oriented elastic side panel 6 from a supply source (not shown).

As housing 140 rotates, the plate 133 holding elastic side panel 6 passes the second station 134 where an adhesive is applied (using nozzles 137 or other suitable device) along upper and lower edges of side panel 6. As housing 140 continues to rotate, plate 133 holding panel 6 passes the third (folding) station 136, which accomplishes a partial and progressive folding of plate 133 and panel 6 using a mechanical linkage capable of opening and closing the plate 133. At this location, fixed cam 142 exerts pressure against spring-loaded clamping bar 135, which causes extension of the clamping bar and folding of plate 133. The progressive folding action continues until the fourth station 138, at which point the clamping bar 135 is completely extended by cam 142, causing vacuum plate 133 to substantially close so that the edges of side panel 6 overlap and are clamped onto the second edges 11 of chassis 4. As housing 140 continues to rotate beyond fourth station 138, the vacuum is removed to release the clamped side panel. The porous plate 133 is again opened due to narrowing of the cam 142 and relaxation of its force on the clamping bar 135. Vacuum is then restored to the porous plate 133 to receive the next side panel at station 132.

It is also within the scope of the invention to employ other bonding techniques including, for instance, thermal heat sealing, ultrasonic bonding, thermal or threaded stitch bonding and the like. Some of these techniques require additional processing and equipment, and a preliminary adhesive bond may be employed to hold the side panels to the chassis prior to and during the additional bonding. The invention covers any process in which edges of seamless side panels are folded over the edges of a folded chassis and bonded.

It is also within the scope of the invention to employ more than one pair of rotary panel applicators along the conveyor; i.e., two or more pairs of panel applicators 110 and 130 along the length of conveyor 102 in FIG. 4. This permits faster overall production speeds and/or slower, more controllable speeds for each pair. If two pairs of panel applicators are used, then each pair would apply side panels to every other chassis. If three pairs of panel applicators are used, then each pair would apply side panels to every third chassis, and so on.

It is also within the scope of the invention to orient the rotary panel applicators at an angle to the conveyor, so that the side panels (i.e., the edges of the side panes) are applied at different angles relative to the chassis. In the embodiment shown in FIG. 4, the rotary panel applicators are positioned to apply the side panels at 90-degree angles relative to the chassis (i.e., relative to the direction of travel of the chassis). By slightly varying the portions of the rotary panel applicators, the side panels may be applied at different angles, for example, at angles of about 90 to 135 degrees relative to the waistline 47 of the chassis, preferably about 90 to 125 degrees, more preferably about 90 to 115 degrees, relative to the waistline. If the absorbent garment of FIG. 2 were modified to incorporate the angular attachment, then the width of the side panels between the attachment seams would, in effect, be narrower toward the waist of the wearer. This angular attachment would cause the garment to fit more snugly at the waist, helping to hold the garment in place on the wearer.

FIGS. 5(a) and 5(b) illustrate embodiments of the absorbent garment 2 in which the edges of side panels 6 and 8 are mounted at different angles relative to waistline 47 on chassis 2. In FIG. 5(a), the side panels 6 and 8 are mounted at a 90-degree angle relative to the waistline. In FIG. 5(b), the side panels 6 and 8 are mounted at a 96-degree angle relative to the waistline. An angle greater than 90-degrees means that the end of each side panel closest to the waistline is disposed inward, so that the unstretched garment narrows toward the waistline.

Figure 1:
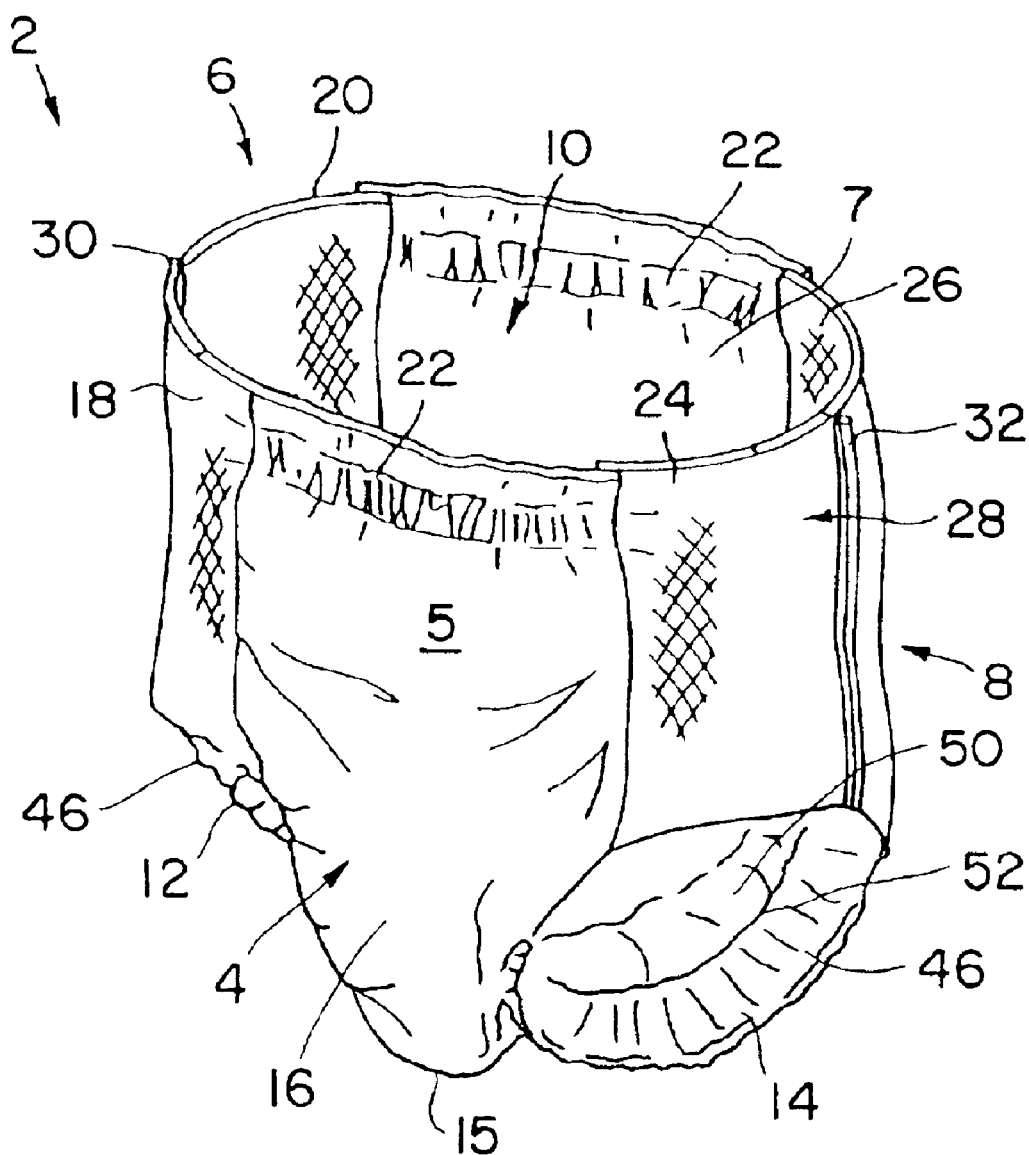
FIG. 1 is a perspective view of a pant-like disposable absorbent article of the prior art.
Figure 2:
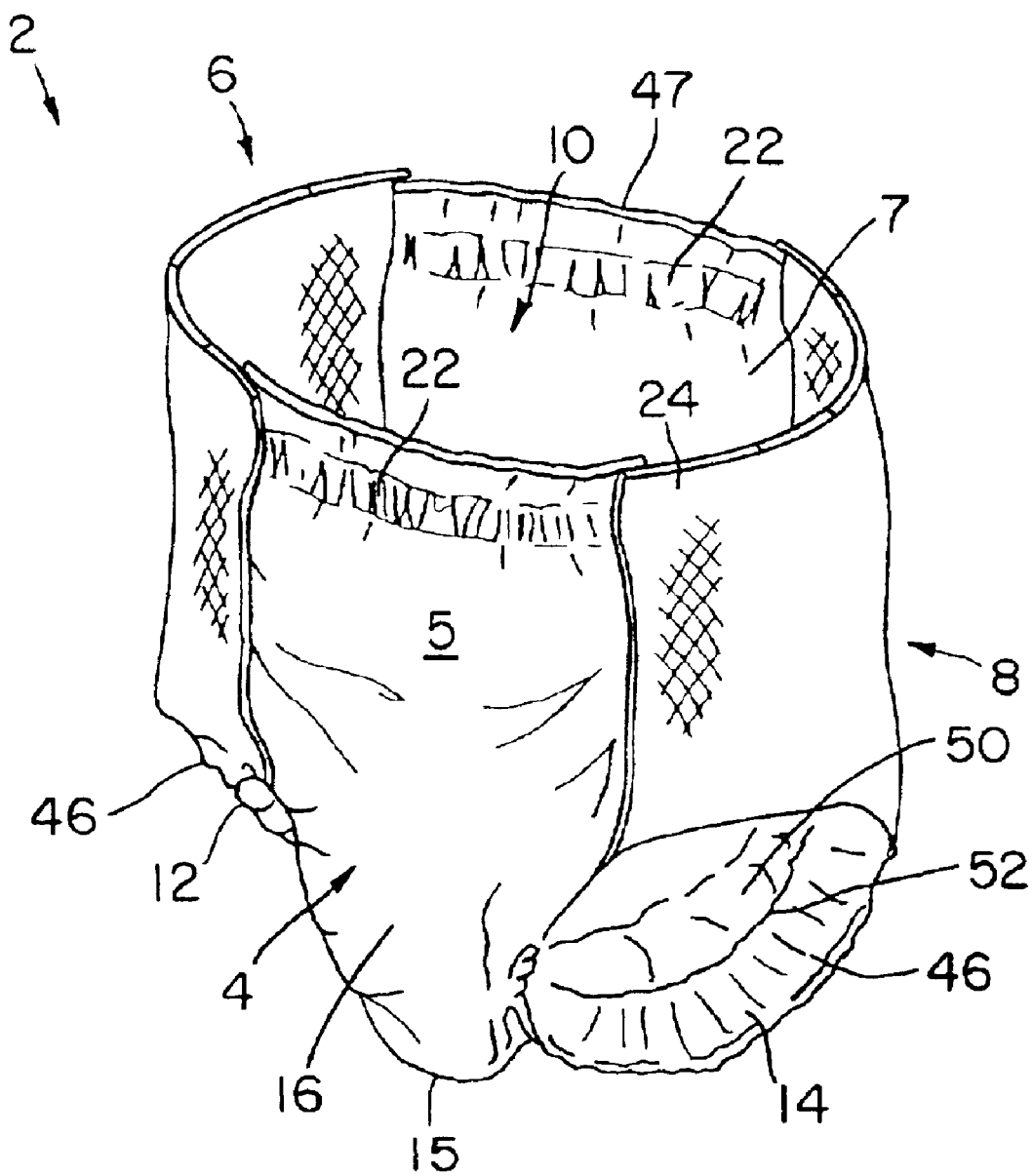
FIG. 2 is a perspective view of a disposable absorbent article of the invention.

The product of the invention is a disposable absorbent garment having single-piece, seamless elastic side panels. Referring to FIG. 2, the disposable absorbent garment includes chassis 4 and two elastic side panels 6 and 8 defining a waist opening 10 and leg openings 12 and 14. Chassis 4, which includes integral front and rear portions 5 and 7 and central region 15, may have a conventional multilayer structure and may be manufactured using conventional techniques prior to being joined to the side panels. A typical chassis may include a liquid-permeable top layer which serves as a bodyside liner, a liquid-permeable surge layer below the top layer, a layer of absorbent material below the surge layer, and a liquid-impermeable outer cover (such as layer 16 in FIG. 2) which prevents leakage from the garment during wear. The outer cover 16 may include more than one layer, such as a liquid-impermeable polyolefin film layer and a polymeric nonwoven filament layer which provides texture and a cloth-like feel to the garment. The layers of chassis 4 may be joined together using adhesives, thermal heat sealing, ultrasonic bonding, stitch bonding, and other conventional techniques.

Outer cover 16 can be made from a wide variety of woven or nonwoven material, films, or a film-coated nonwoven material, including for instance cast or blown films of polyethylene, polypropylene, polyester or blends thereof. Outer cover 16 may also be a composite of a bonded carded or spunbonded or meltblown material, for example, a spunbonded-meltblown composite of thermoplastic material or a spunbonded-meltblown-spunbonded thermoplastic material, wherein the spun-bonded layer can provide a cloth-like texture and the meltblown layer can provide liquid impermeability. Materials of which outer cover 16 can be made include nonwovens having a high basis weight, such as about 0.4 ounces per square yard or greater. Outer cover 16 can also include extruded films of polyolefin polymers or copolymers, or other thermoplastic materials. Generally outer cover 16 will have a length from about 12 inches (300 mm) to about 30 inches (760 mm), and a width from about 3 inches (75 mm) to about 20 inches (500 mm), depending on the size of the garment.

The absorbent layer can be made of wood pulp fluff or a mixture of wood pulp fluff and a superabsorbent material, or a wood pulp fluff integrated with a thermoplastic absorbent material treated with a surfactant. Thermal binders, such as Pulpex® can be used in blends or layering with the fluff and superabsorbent. The absorbent layer can also be a batt of meltblown synthetic fibers, a bonded carded web of synthetic or natural fibers or blends thereof, a composite of meltblown fibers and the like. The synthetic fibers can be, but are not limited to, polypropylene, polyethylene, polyester and copolymers of these or other polyolefins.

The term "superabsorbent" or "superabsorbent material" refers to a water-swellable, water-insoluble organic or inorganic material capable, under the most favorable conditions, of absorbing at least about 20 times its weight and, more desirably, at least about 30 times its weight in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations or Van der Waals forces.

Examples of synthetic superabsorbent material polymers include the alkali metal and ammonium salts of poly(acrylic acid) and poly(methacrylic acid), poly(acrylamides), poly(vinyl ethers), maleic anhydride copolymers with vinyl ethers and alpha-olefins, poly(vinyl pyrrolidone), poly(vinylmorpholinone), poly(vinyl alcohol), and mixtures and copolymers thereof. Further superabsorbent materials include natural and modified natural polymers, such as hydrolyzed acrylonitrile-grafted starch, acrylic acid grafted starch, methyl cellulose, chitosan, carboxymethyl cellulose, hydroxypropyl cellulose, and the natural gums, such as alginates, xanthan gum, locust bean gum and the like. Mixtures of natural and wholly or partially synthetic superabsorbent polymers can also be useful in the present invention. Other suitable absorbent gelling materials are disclosed by Assarsson et al. in U.S. Pat. No. 3,901,236 issued Aug. 26, 1975. Processes for preparing synthetic absorbent gelling polymers are disclosed in U.S. Pat. No. 4,076,663 issued Feb. 28, 1978 to Masuda et al. and U.S. Pat. No. 4,286,082 issued Aug. 25, 1981 to Tsubakimoto et al.

Both the surge layer and bodyside liner are constructed from highly liquid pervious materials. These layers function to transfer liquid from the wearer to the absorbent layer. Suitable materials include porous woven materials, porous nonwoven materials, and apertured films. Examples include, without limitation, any flexible porous sheets of polyolefin fibers, such as polypropylene, polyethylene or polyester fibers; webs of spunbonded polypropylene, polyethylene or polyester fibers; webs of rayon fibers; bonded carded webs of synthetic or natural fibers; or combinations thereof. Either layer may also be an apertured plastic film. The various layers of chassis 4 have dimensions which vary depending on the size and shape of the wearer.

The stretchable side panels 6 and 8 can be constructed of conventional woven or nonwoven materials, constructed from a wide variety of elastic and stretchable polymers. The terms "elastic" and "stretchable" include any material which can be stretched, and which tends to return to its original shape when relaxed. Suitable polymers include without limitation block copolymers of polystyrene, polyisoprene and polybutadiene; copolymers of ethylene, natural rubbers and urethanes; and combinations of the foregoing. Particularly suitable are styrene-butadiene block copolymers sold by Shell Chemical Company under the trade name KRATON®. Other suitable polymers include copolymers of ethylene, including without limitation ethylene vinyl acetate, ethylene methyl acrylate, ethylene ethyl acrylate, ethylene acrylic acid, stretchable ethylene-propylene copolymers, and combinations thereof. Also suitable are co-extruded composites of the foregoing, and elastomeric staple integrated composites where staple fibers of polypropylene, polyester, cotton and other materials are integrated into an elastomeric meltblown web. Certain elastomeric single-site or metallocene-catalyzed olefin polymers and copolymers are also suitable for the side panels.

The elastic side panels 6 and 8 may be attached to the chassis 4 using a wide variety of conventional adhesives. Suitable adhesives include hot melt adhesives, spray adhesives, self-adhering elastomeric materials, and the like. As explained above, the bonding between overlapping edges of the chassis and side panels may be augmented using thermal bonding, ultrasonic bonding, stitch bonding, and the like.

Figure 3:
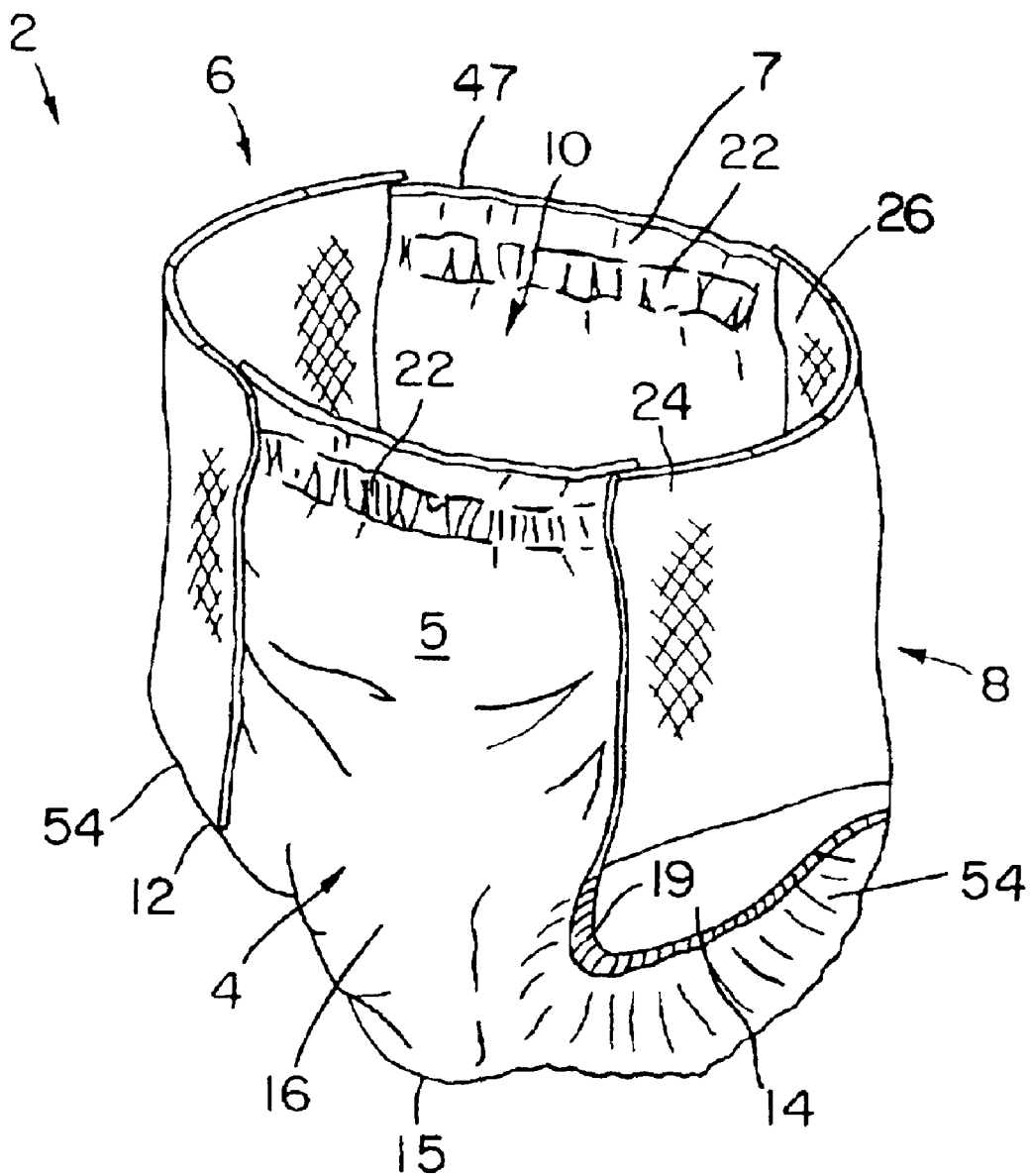
FIG. 3 is a perspective view of another embodiment of a disposable absorbent article of the invention.

In order to prevent leakage from the leg openings during wear, the absorbent garments of the invention may be provided with leak guards. FIGS. 2 and 3 (in which like elements have the same reference numerals) illustrate two different embodiments of the leak guards. In the garment of FIG. 2, conventional leg openings 12 and 14 have elastic bands 46 attached around their edges. In order to prevent leakage from the leg openings, elastic flaps 50 are attached at seams 52 to the inside of the chassis 4, around the lower portions of the leg openings. In the garment of FIG. 3, the separately attached elastic flaps have been eliminated. Instead, the leak guards 54 are provided by extending the outer cover 16 substantially beyond the inner absorbent layer so that pouches are formed between the absorbent layer and the leg openings. Each leak guard 54 is equipped with one or more elastic bands 19 aligned with its edge, to maintain the leak guard in an upright position during wearing of the garment, and to form an effective seal around the leg.

The elastic bands 46 and 19 may be in the form of single or multiple bands per leg. A wide variety of elastic materials may be employed. Examples include a film or meltblown web formed using block or graft copolymers of butadiene, isoprene, styrene, ethylene-methyl acrylate, ethylene-vinyl acetate, ethylene-ethyl acrylate or blends thereof. One preferred elastomeric is a block copolymer of styrene-ethylbutadiene-styrene. Specific materials of which elastic bands 19 can be made are the KRATON G series from Shell Chemical Company, such as Kraton G-1650, Kraton G-1652, Kraton GX-1657 and preferably Kraton G-2740X. Also, the Kraton D series can be used, as well as polyester elastomeric materials, polyurethane elastomeric materials and polyamide elastomeric materials. Elastomeric single-site or metallocene-catalyzed olefin polymers and copolymers can also be employed. Also, elastic bands 46 and 19 can be made of an activatable material applied in an unstretched condition, and activated by heat, light, moisture or radiation to cause shrinkage and elasticity. Activatable elastic materials can be obtained from the 3M Company. The elastic bands 46 and 19 may be attached at or inward from the edges of the chassis at the leg openings using a variety of conventional techniques including adhesive bonding, thermal bonding, ultrasonic bonding, stitch bonding and the like.

Referring again to FIGS. 2 and 3, the chassis 4 also may have elasticized waist portions 22 in the front and back of the garment. Elasticized waist portions 22 may be formed of single or multiple bands, may be made of the same or different materials as elastic bands 46 and 19, and may be affixed using the same or similar conventional techniques.

The product of the invention is a pant-like disposable absorbent garment which can be properly sized and used as a diaper, swim suit, child training pant, adult incontinence garment, or similar pant-like absorbent garment. The seamless elastic side panels facilitate reduced manufacturing cost and improved aesthetic appearance.

While the embodiments of the invention described herein are presently preferred, various modifications and improvements can be made without departing from the spirit and scope of the invention. The scope of the invention is indicated by the appended claims, and all changes that fall within the meaning and range of equivalents are intended to be embraced therein.

We claim:

1. A pant-like disposable absorbent garment, comprising:
   a chassis including at least a liquid-permeable bodyside liner, an absorbent layer, and a substantially liquid-impermeable outer cover;
   a first seamless single-piece side panel overlapping and bonded to a first edge of a front portion of the chassis and to a first edge of a back portion of the chassis using bonds to both first edges selected from the group consisting of adhesive bonds, thermal bonds, ultrasonic bonds, stitch bonds, and combinations thereof; and a second seamless, single-piece side panel overlapping and bonded to a second edge of the front portion of the chassis and to a second edge of the back portion of the chassis using bonds to both second edges selected from the group consisting of adhesive bonds, thermal bonds, ultrasonic bonds, stitch bonds, and combinations thereof.

2. The disposable absorbent garment of claim 1, wherein the first and second seamless side panels comprise an elastic material.

3. The disposable absorbent garment of claim 1, wherein the chassis and seamless side panels define a waist opening and first and second leg openings.

4. The disposable absorbent garment of claim 1, wherein the first and second side panels are bonded to the chassis using an adhesive.

5. The disposable absorbent garment of claim 1, wherein the first and second side panels are bonded to the chassis by thermal heat sealing.

6. The disposable absorbent garment of claim 1, wherein the first and second side panels are bonded to the chassis using ultrasonic bonds.

7. The disposable absorbent garment of claim 1, wherein the edges of the first and second side panels are at angles of about 90–135 degrees relative to a waistline of the chassis.

8. The absorbent garment of claim 7, wherein said angle is about 90–115 degrees.

9. The disposable absorbent garment of claim 1, wherein the first and second side panels are bonded to the chassis using thermal stitch bonds.

10. The disposable absorbent garment of claim 1, wherein the first and second side panels are attached to the chassis using threaded stitch bonds.

11. The disposable absorbent garment of claim 1, comprising a child training pant.

12. The disposable absorbent garment of claim 1, comprising an adult incontinence garment.

13. The disposable absorbent garment of claim 1, comprising swim wear.

\* \* \* \* \*